United States Patent
Bell

(10) Patent No.: US 6,551,788 B1
(45) Date of Patent: Apr. 22, 2003

(54) PARTICLE-BASED LIGAND ASSAY WITH EXTENDED DYNAMIC RANGE

(75) Inventor: Michael L. Bell, Fullerton, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/995,520

(22) Filed: Nov. 28, 2001

(51) Int. Cl.[7] .............................................. G01N 33/53
(52) U.S. Cl. ........................ 435/7.1; 435/810; 435/7.92; 436/523; 436/172; 436/517; 436/518
(58) Field of Search .............................. 435/7.1, 6, 808, 435/810; 436/518, 524, 525, 526, 527, 825, 523, 172, 533, 517, 805

(56) References Cited

U.S. PATENT DOCUMENTS

| 5,420,016 A | * | 5/1995 | Boguslaski et al. ............ 435/12 |
| 5,567,627 A | | 10/1996 | Lehnen ....................... 436/518 |
| 5,585,241 A | | 12/1996 | Lindmo ......................... 435/6 |
| 5,723,346 A | | 3/1998 | Frengen ...................... 436/523 |
| 5,739,042 A | | 4/1998 | Frengen ...................... 436/523 |
| 5,851,777 A | * | 12/1998 | Hunter et al. ................. 435/7.1 |
| 6,165,739 A | * | 12/2000 | Clatch et al. .................. 435/29 |
| 6,200,820 B1 | | 3/2001 | Hansen ....................... 436/523 |
| 6,248,597 B1 | * | 6/2001 | Eda et al. .................... 436/518 |
| 6,327,410 B1 | * | 12/2001 | Walt et al. ................... 385/115 |

FOREIGN PATENT DOCUMENTS

| GB | WO 89/11101 | * | 5/1989 |

* cited by examiner

Primary Examiner—Long V. Le
Assistant Examiner—Gary W. Counts
(74) Attorney, Agent, or Firm—Hogan & Hartson LLP; William H. May; D. David Hill

(57) ABSTRACT

This invention relates to methods of assaying one or more analytes simultaneously. The assays of this invention are capable of providing wide dynamic range and rapid processing times. A wide dynamic working range is achieved by simultaneously incubating a sample which may contain the analyte(s) of interest with two or more independently determinable classes of particles coated with an analyte-specific binding partner. The two or more particle classes differ from each other at least in size. The analyte concentration is obtained from readings derived from these two classes by means of a combined standard curve.

41 Claims, No Drawings

PARTICLE-BASED LIGAND ASSAY WITH EXTENDED DYNAMIC RANGE

FIELD OF THE INVENTION

This invention relates to reagents and methods for rapidly and quantitatively assaying the concentration of analytes in biological samples. More particularly, this invention provides assays having a wide dynamic working range by simultaneously incubating a sample which may contain the analyte(s) of interest with two or more independently determinable classes of a solid-supported binding partner.

BACKGROUND OF THE INVENTION

Assay techniques for determining the presence, desirability, and the concentration of an analyte using a binding partner having specificity for that analyte are frequently encountered, e.g., in the fields of biochemistry and clinical chemistry. Thus, for example, a wide range of immunological and related techniques has been proposed for determining materials, such as antigens in serum, using an appropriate binding partner for the analyte, such as a specific antibody, e.g., a monoclonal antibody, for a particular antigen.

One such technique comprises competitive binding assays, in which a known amount of a labeled version of an analyte to be determined, e.g., carrying a radioactive label, or its analogue and a relatively small known amount of a binding partner specific for the analyte are incubated with the analyte to be determined, whereby the labeled and the naturally occurring analyte compete for the binding partner. The amount of labeled analyte bound to the binding partner is inversely related to the concentration of analyte in the sample.

Another useful technique comprises sandwich assays. These employ an excess of the binding partner that binds to the analyte in the sample. A labeled second ligand is also added and binds to the captured analyte forming a sandwich, with the amount of label dependent on the amount of analyte captured. The amount of bound and labeled analyte is directly related to the concentration of analyte in the sample. The binding partner and the labeled ligand in such sandwich assays preferably have affinities for different binding sites, e.g., epitopes, on the analyte. The ligand may, for example, be labeled for reading on the basis of radioactivity, light absorption, or fluorescence.

Sandwich assays tend to exhibit greater sensitivity than competitive binding assays and are, therefore, usually preferred. It will be appreciated that high sensitivity is essential in, for example, immunoassays in clinical laboratories, where it maybe required to quantify, e.g., antigens present in the serum at concentrations in the nmol/l to pmol/l range or even lower. However, the sandwich assay requires the presence of two binding sites on the analyte. Therefore, the competitive format is preferred for smaller molecules where two binding sites may not be present or may be sterically hindered.

The binding partner in both of the above-described types of assays is commonly coupled to a solid support in order to facilitate isolation of the bound analyte and the competing or analyte-bound label. Thus, for example, the binding partner may be coupled to the surface of a reaction vessel, e.g., to the surfaces of the wells of a microtitre plate made from a suitable plastics material, so as to facilitate washing to remove unbound excess labeled ligand.

Alternatively, the binding partner may be coupled to the surfaces of an array of particles, for example, made of a suitable plastics material, such as polystyrene or polyacrylate. The separation of the bound analyte/label from the free label may then be affected by, for example, filtration or, in the event that superparamagnetic particles are employed, by the application of a magnetic field. The particles are advantageously of microscopic size in order to present a large total surface area coated with the binding partner. The use of monosized microparticles is preferred since it ensures that the particles exhibit standard binding properties.

An immunoassay for bead-based multiplexing uses coded particles with distinguishable optical characteristics (such as bead size, bead number, or incorporation of one or more fluorescent dyes). Particles with the same code receive the same ligand (e.g., antibody) on their surface and are thus responsive to the same analyte.

A disadvantage of the above-described basic assay techniques is that separation of the bound analyte and label and associated washing steps to remove the unbound label are inherently time-consuming and labor-intensive. It is known, however, that this problem may, in principle, be avoided in the case of particle-based assays if the particles are analyzed by means of flow cytometry. This typically involves the passage of a suspension of particles through the measurement region of a photometer in such a way that successive individual particles are irradiated with excitation light, causing the emission of a pulse of scattered light related to the size of the particle and a further signal, e.g., a pulse of fluorescent light, related to the amount and nature of the label bound to the particle. Accordingly, there is no need to separate unbound label prior to the flow cytometric particle analysis, which is therefore said to be a homogeneous, i.e., separation-free, assay.

A general problem associated with clinical assays especially immunoassays, using the above assay formats is that many analytes have wide clinical ranges. Thus, the signal response of such assays frequently saturates below the maximum clinical value. Specimens giving a saturated signal in such assays are typically diluted and rerun so that the assay range may cover more clinical values. Such a strategy is reasonable for single assays where the frequency of dilution and rerun is low. However, when a specimen is assayed for several analytes, the likelihood of needing to re-assay the specimen for a particular analyte increases. Since dilutions and reruns tie up system resources, an alternative method is needed for dealing with wide clinical range analytes in specimens.

U.S. Pat. No. 5,585,241 describes an assay technique that utilizes high and low affinity-binding partners, respectively, coated onto different types of monodisperse particles that are distinguishable by flow cytometry. Predetermined amounts of this binary particle mixture and of labeled ligand are incubated with the analyte, and the resulting two types of labeled ligand-carrying particles are thereafter independently, but simultaneously, detected by means of a flow cytometer, the analyte concentration being determined from the thus-obtained two measurement values by reference to a double standard calibration curve. However, this method requires the production or acquisition of two different types of binding partners (ligands) for the analyte. Further, each particle type requires a separate coupling reaction to attach the binding partner to the particle in addition to optimization of each of these coupling reactions.

U.S. Pat. No. 5,739,042 describes an assay in which two solid forms of binding partner are reacted successively, rather than simultaneously, with an analyte and a labeled ligand. The addition of the second form of the solid form of binding partner prevents any further binding of the analyte to the first form of solid binding partner and thus acts as a type of washing step in which the unbound analyte is "washed away" and thus effectively quenches the reaction. This method thus has the disadvantages of requiring an additional reagent delivery step. This step requires either associated hardware or a throughput time slice, both of which increases the cost required per unit of assay throughput.

There still exists a need for a cost-effective method of assaying one or more analytes in a sample without the need for sample dilution and rerunning the assay, and which provides for an extended dynamic range.

SUMMARY OF THE INVENTION

This invention relates to methods of assaying one or more analytes in a sample. More specifically, this invention provides assays that are capable of providing a wide dynamic range and rapid processing times, and eliminates the need for multiple sample dilutions and assay reruns.

Accordingly, one aspect of this invention provides a method for assaying an analyte in a sample, comprising:
  a) providing a set of coated particles comprising at least
    i) a first class of particles having a first binding partner for the analyte immobilized thereon, and
    ii) a second class of particles having the first binding partner for the analyte immobilized thereon, wherein the first and second classes of particles are independently determinable, and wherein the particles of the first class are smaller than the particles of the second class;
  b) simultaneously incubating the sample in the presence of the set of particles under conditions that allow the formation of a first complex comprising the sample analyte bound to the first binding partner immobilized on the first class of particles and/or a second complex comprising the sample analyte bound to the first binding partner immobilized on the second class of particles; and
  c) determining the amount of the first complex and/or the second complex, wherein the amounts are determinative of the concentration of the analyte in the sample.

In one embodiment, the assay is a sandwich assay, wherein the method further comprises incubating the sample and the set of coated particles with a ligand comprising a labeled second binding partner for the analyte.

In another embodiment, the assay is a competitive assay, wherein the method further comprises incubating the sample and the set of coated particles with a ligand comprising a labeled analogue of the analyte.

The methods of this invention can be used to assay a single analyte or multiple analytes simultaneously.

Additional advantages and novel features of this invention shall be set forth in part in the description that follows, and in part will become apparent to those skilled in the art upon examination of the following specification or may be learned by the practice of the invention. The novel features and advantages of the invention may be realized and attained by means of the instrumentalities, combinations, and methods particularly pointed out in the appended claims.

DETAILED DESCRIPTION OF THE INVENTION

This invention relates to methods of assaying one or more analytes simultaneously. The assays of this invention are capable of providing a wide dynamic range and rapid processing times. The assays of this invention eliminate the need for multiple sample dilutions and sample reruns. Further, the methods of this invention eliminate extra reagent addition steps, thus reducing the cost of the assay.

The present invention is based on the surprise finding that a wide dynamic working range may be achieved by simultaneously incubating a sample which may contain the analyte(s) of interest with two or more independently determinable classes of particles coated with an analyte-specific binding partner. Preferably, the particles in each class are coated with the same binding partner. The two or more classes of particles differ from each other at least in size. The analyte concentration is obtained from readings derived from these two classes by means of a combined standard curve.

Conventional particle-based assays use a capture-binding partner, such as antibody or antigen in the case of an immunoassay, coated on the surface of particles, such as small beads. The beads are deliberately made as similar to each other as possible to improve assay precision.

In contrast, the method of this invention uses a set comprising at least two classes of particles coated with a binding partner for an analyte of interest, wherein the size of the particles in one class differs from the size of particles in the other classes in order to extend the dynamic range. The reaction proceeds independently of the two or more classes of particles without a significant change in the free analyte concentration. The mechanism of action relies on diffusion-limited kinetics, where a larger particle has more ready access to slowly diffusing analyte molecules than does a smaller particle. For example, larger particles give more signal at low analyte concentrations but saturate at high concentrations. Smaller particles give signals that may be too small to reliably measure at low analyte concentrations but produce readable signals at higher analyte concentrations. The difference in the amount of analyte captured per particle arises from the kinetics of the binding reaction rather than from the different affinities of the binding partners. Comparison of the signals from the at least two sizes of particles produces an extended dynamic range. By combining signals from two or more different size particles, the total measurable range may be increased. Thus, in the method of this invention, the difference in sizes between the different classes of particles is key to the functionality of the assay and not just as a means to distinguish the particles during detection.

Since the two or more classes of particles coated with analyte-specific binding partner are added to the reaction mixture simultaneously, one advantage of the method of this invention is that it eliminates an additional reagent delivery step as performed in other methods in the art. This additional step requires either associated hardware or a throughput time slice, each of which increases the cost required per unit of assay throughput. Since clinical chemistryand biopharmaceutical testing are both very cost sensitive, the cost savings of this invention provide a clear advantage over methods currently used in the art.

Accordingly, one embodiment of this invention provides a method for assaying an analyte in a sample, comprising:
  a) providing a set of coated particles comprising at least
    i) a first class of particles having a first binding partner for the analyte immobilized thereon, and
    ii) a second class of particles having the first binding partner for the analyte immobilized thereon, wherein the first and second classes of coated particles are independently determinable, and wherein the particles of said first class are smaller than the particles of the second class;

b) simultaneously incubating the sample in the presence of the set of particles under conditions that the allow formation of a first complex comprising the sample analyte bound to the first binding partner immobilized on the particles of the first class and/or a second complex comprising the sample analyte bound to the binding partner immobilized on the particles of the second class; and c) determining the amount of the first complex and/or the second complex, wherein the amounts are determinative of the concentration of the analyte in the sample.

In one embodiment, the assay is a sandwich assay, wherein a known amount of a ligand comprising a labeled second binding partner for the analyte is incubated with the sample and the set of coated particles. The ligand binds to the analyte of the first and/or second complex to form first and/or second sandwich complexes, respectively. In this embodiment signals produced by the labels in the sandwich complexes are directly related to the concentration of the sample analyte.

In another embodiment, the assay is a competitive assay, wherein a known amount of a ligand comprising a labeled analogue of the analyte is incubated with the sample and the set of coated particles. The ligand competes with the analyte for binding the first binding partner and forms a third complex comprising the ligand bound to the binding partner on the particles of the first class and a fourth complex comprising the ligand bound to the binding partner on the particles of the second class. In this embodiment, signals produced by the labels bound to the third and/or fourth complexes are inversely related to the concentration of the sample analyte.

In both the sandwich assay and the competitive assay format, the analyte concentration is obtained by reference to a combined calibration curve as discussed below.

In one embodiment, the extended dynamic range feature of this invention is accomplished by providing a set comprising two or more classes of particles, wherein the particles in each class are coated with the same binding partner to the same analyte. The particles of each class differ from the particles of the other classes at least in size. The different classes may also differ from each other in that the particles of each class may have different codes associated with them, such as distinguishable and detectable dyes that are loaded into the particle material. Thus, the codes may be another means of distinguishing between the different particle classes in addition to the differences in size. Alternatively, the classes may differ from each other in that the particles of one class.may be made from a different material than the particles of the other classes. In either case, a cytometer can determine the number of the particles of each class based on the optical signals produced by the different size particles and the different codes. In addition, the cytometer can detect the labels of the labeled ligands that are part of a sandwich complex or that become bound to the particles of each class. The cytometer can associate signals due to labels with individual particles and with each of the different classes by combining the signals from all the individual particles of a particular class.

In one embodiment, the analyte-specific binding partner is immobilized on two or more classes of particles, wherein the particles of all classes are made from the same type of material, e.g., the particles in each class are polymer particles, such as polystyrene particles, and where the particles of the two or more classes differ is size, e.g., the first class comprises particles that are smaller in diameter than the particles of the second class. Further, the particles of one or more classes may be loaded with distinguishable dyes, e.g., the dye loaded in the particles of one class of particles is different than the dye loaded into the other classes. Suitable dyes that may be loaded into the particles include, but are not limited to, cyanine dyes, BODIPY dyes, fluorescein derivatives, and rhodamine derivatives.

In another embodiment, the analyte-binding partner may be immobilized on two or more classes of particles, wherein each class comprises particles made of a material that is different than the particles of another class. For example, one class of particles may comprise polystyrene particles and another class of particles may comprise gold particles. In this embodiment, the particles in one class differ in size from the particles in each of the other classes. In all embodiments, the size difference is primarily directed to produce a difference in the amount of analyte captured.

In one embodiment, the method of this invention uses a single analyte-specific binding partner immobilized on two or more classes of particles to capture an analyte of interest. This embodiment therefore requires only a single development effort to procure the binding partner and to optimize the reaction for coupling the binding partner to the particle. However, the invention is not limited to the use of one binding partner per analyte. Thus, in other embodiments, particles of each class may be coated with a different binding partner, wherein all the binding partners in the set of coated particles are specific for the same analyte of interest.

The term "coated particle," as used herein, refers to an carrier particle having an analyte-specific binding partner immobilized or coated thereon, where the binding partner is attached to the particle by covalent (chemical) bonds or non-covalent bonds, e.g., physical adsorption, or by indirect attachment.

As used herein, the term "set" refers to a collection of two or more classes of particles having immobilized thereon a binding partner for the same analyte of interest. The binding partner coated on the particles of one class may be the same as the binding partner coated on the particles of the other classes. Alternatively, particles of each class are coated with a different binding partner, provided that each binding partner is specific for the same analyte.

The term "class" refers to particles belonging to a specific distinguishable group. The particles of a specific class are made from the same material and are substantially the same size. If labeled, the particles of a specific class all contain the same label or other code. Thus, a set may comprise a first class and a second class of particles, wherein the particles of the first and second classes are coated with the same binding partner, but wherein the particles of the first class is distinguishable from the particles of the second class.

The term "binding partner" or "specific binding partner," as used herein, refers to a molecule or moiety that specifically recognizes and binds to the analyte of interest or an analogue of the analyte, and exhibits negligible cross-reactivity with other molecules or substances that may be present in the sample being tested. Typical binding partners include, but are not limited to, antigens, antigen fragments, receptors, nucleic acids, and polyclonal antibodies, monoclonal antibodies, antibody fragments, lectins, protein A, protein G, polypeptides, avidin, streptavidin, cyclodextrans, and crown ethers, intrinsic factor, folate and binding protein. A binding partner specific for a given analyte may be obtained from commercial sources or may be prepared in accordance with standard procedures known to those skilled in the art. Examples of analyte:binding partner pairs include, but are not limited to, hapten:antibody, biotin:avidin, hormone:receptor, polypeptide:antibody, and oligonucleotide:complementary DNA or RNA.

As used herein, an "analyte" or "analyte of interest" refers to the substance whose presence and/or concentration in a sample is to be determined. The term "analyte" includes any substance for which there exists a specific binding partner, or for which a specific binding partner can be prepared. Representative analytes include, but are not limited to, drugs, antigens, haptens, antibodies, proteins, peptides, amino acids, hormones, receptors, enzymes, lectins, carbohydrates, steroids, cancer cell markers, tissue cells, viruses, vitamins, nucleic acids, and pesticides.

The term "antibody," as used herein, refers to immunoglobulins that are produced in response to the detection of a foreign substance, and includes intact molecules as well as functional fragments thereof, such as Fab, F(ab')$_2$, and Fv.

By "analyte analogue," it is meant any molecule or chemical entity that is able to bind or has a specific binding affinity to a specific binding partner for the analyte of interest which is comparable to the binding affinity of the analyte. An analyte analogue differs from an analyte in that it is not normally present in the sample being tested and that it has some feature that allows its presence to be detected. Such feature is typically a label such as a radioactive atom, an enzyme, dye, substrate, linker, or a solid phase. An analyte analogue normally comprises a portion that is similar to the structure of the analyte and a portion that is different in order to facilitate its detection. Analyte analogues are most commonly employed in competitive assays for the detection of small molecules.

To conduct an assay of the present invention, it is necessary to provide a set of coated particles comprising at least a first and second class of particles having immobilized thereon an analyte-specific binding partner. The binding partner may be immobilized or bound to the particles through chemical methods (i.e., covalent bonds) through non-chemical methods, such as physical adsorption (i.e., through non-covalent bonds, such as hydrophobic and charge interactions), and through indirect methods. Such methods are well known to those skilled in the art.

Suitable materials for the particles to be coated include, but are not limited to, naturally occurring and synthetic organic polymers, such as polysaccharides, styrene polymers, polyacrylates (e.g., polyacrylamide and hydroxyethyl polymethacrylates), glass, ceramic, carbon, polyvinyl chloride, protein, and the like. Styrene polymers include polystyrene, polymers containing aromatic moieties, and higher aromatic compounds, such as naphthalene, anthracene, etc. In one embodiment, the particles are latex beads. Other suitable particle materials include metallic particles, such as gold particles, colloidal metals, and colloidal and metal oxides.

Particles of different sizes and materials are commercially available. The appropriate size for the two classes of particles depends on the dynamic range of the analyte. In general, all particles preferably have diameters in the range of 1 to 20 micrometers. The size of the signal developed depends on the surface area of the particle, which scales as the square of the diameter. For example, a 10-micrometer spherical particle has twice the surface area, i.e., 314 $\mu m^2$ of a 7-micrometer diameter bead having a surface area of 154 $\mu m^2$, and therefore would develop roughly twice the signal in an assay. To be useful, the signal ratio between the two particle classes is preferably in the range of 2 to 16. This means that their diameters preferably are in the ratio of about 1:1.4 to 1:4. For example, if the diameter of the smaller particles is 3 micrometers, then the diameter of the larger particles is preferably in the range of 4 to 12 micrometers.

In a sandwich assay format of this invention, once the two or more classes of particles coated with the analyte-binding partner are provided, the assay comprises incubating the sample simultaneously in the presence of the first and second classes of the coated particles and known amounts of a labeled ligand comprising a second binding partner specific for the analyte of interest. The mixture is incubated under conditions that allow the formation of a first sandwich complex comprising the sample analyte bound to the first binding partner of the first class of particles and the labeled ligand, and/or a second sandwich complex comprising the sample analyte bound to the first binding partner of the second class of particles and the labeled ligand. Such incubation conditions are well known to those skilled in the art and need not be described further. The labeled ligand provides one means of detecting the first and/or second sandwich complexes. That is, the labeled ligand of the first complex will produce a first distinguishable signal, and the labeled ligand of the second complex will produce a second distinguishable signal. The first and second signals are directly related to the concentration of the analyte in the sample.

In a competitive assay format of this invention, a set comprising two or more classes of the particles coated with a binding partner for the analyte of interest is incubated simultaneously with the sample and with known amounts of a labeled ligand comprising a second binding partner specific for the analyte of interest. In the competitive assay, the labeled ligand competes with the analyte in the sample for binding to the first binding partner. The mixture is incubated under conditions that allow the formation of various complexes. Thus, in addition to the formation of first and second complexes comprising the analyte bound to the binding partner on the first and second classes of particles, respectively, a third complex comprising the first binding partner of the first class of particles bound to the labeled ligand, and/or a fourth complex comprising the first binding partner of the second class of particles bound to the labeled ligand are also formed. The label of the third complex will produce a first signal, and the label of the fourth complex will produce a second signal, wherein the first and second signals are inversely related to the concentration of the analyte in the sample.

As used herein, the term "ligand" refers to a chemical moiety that either specifically binds to the analyte (in the case of a sandwich assay) or to the analyte-binding partner (in the case of a competitive assay). The ligand may be naturally occurring or it may be artificially prepared. This invention utilizes a labeled ligand as one means of detecting the various complexes formed in the assays. The labeled ligand is normally employed in a predetermined amount and has an affinity for the first binding partner (in the case of a competitive binding assay), or for the analyte in the case of a sandwich assay. In the latter type of procedure, the labeled ligand and the first binding partner preferably attach to different binding sites, e.g., epitopes, on the analyte.

The methods of this invention may also be used for the simultaneous assay of a plurality of analytes, by using the appropriate numbers of sets of coated particles and the appropriate number of second binding partners (for sandwich assays) or the appropriate umber of labeled analyte analogs (for competitive assays). More specifically, this invention provides a method of assaying multiple analytes simultaneously, wherein the method first comprises providing a plurality of sets of coated particles equal to the number of analytes to be assayed. In this method, each set of coated particles is specific for a particular analyte of interest and is separately determinable. Each set of coated particles for a particular analyte to be assayed comprises at least a first class of particles coated with a first binding partner for a set-specific analyte, and a second class of particles coated with a first binding partner for the same set-specific analyte, wherein the first and second classes within each set are independently determinable. In each set, the particles of one class are larger than the particles of the other class.

The sample is simultaneously incubated in the presence of the sets of coated particles under conditions that allow the formation of a set of complexes for each analyte of interest. Each set of complexes per analyte comprises a first complex comprising the set-specific analyte bound to the first binding partner immobilized on the particles of the first class, and/or a second complex comprising the set-specific analyte bound to the first binding partner immobilized on said particles of the second class.

After a predetermined incubation period, the amounts of each of the first and/or said second complexes formed by each set of coated particles are measured, wherein the amounts are determinative of the concentrations of the analytes in the sample.

It is necessary when a plurality of analytes is to be assayed simultaneously that all the individual classes are separately distinguishable, e.g., by flow cytometry. For example, the second binding partners or the labeled analogues can be labeled with different labels, e.g., with moieties having different colors of fluorescence, in order to quantify different amounts of the various analytes in the sample.

The protocol for the assays of this invention can be varied widely, depending upon the system being employed, the sensitivity of the assay, the speed with which the assay is to be carried out, the nature of the analyte, and the like. As stated above, the assays comprise combining the two or more classes of coated particles simultaneously with the sample. The combined particle classes can be combined with the sample and the labeled ligand concomitantly or sequentially.

In one embodiment of the present invention, flow cytometry is used to detect the formation of, and optionally quantify, the complexes and relate the information to the detection and determination of the amount of an analyte of interest present in the sample. Alternatively, other particle-reading systems, such as scanning cytometers, may be used.

The methods of this invention for performing simultaneous analyses of multiple analytes rely upon the capability of a flow cytometer to simultaneously record side scatter and/or forward scatter of reflected light and light emitted from labeled ligands. When a flow cytometer is used, the particles are read one at a time while flowing single file in a sheathed stream through a flow cell. In one embodiment, the labeled ligand comprises a fluorescent moiety to provide a detectable label upon excitation of the fluorescent moiety with energy of the appropriate wavelength. The particles are read one at a time by measuring the identifying characteristics, e.g., size, material, label, etc., that identify the class to which each particle belongs, and by measuring the analytical signal from each particle, i.e., that measure the label. The particles encounter excited light that is re-emitted and impinges on a number of detectors. The position and wavelength response range of these detectors enables determination of several parameters simultaneously. These parameters include the intensity of forward scatter and side scatter of reflected laser light, which is determined by the size of the particle in the light path, and the intensity of fluorescent light emitted at right angles to the light path, which is a function of the quantity of fluorescent moiety on the ligand. Thus, both the size of the particles and fluorescence of the fluorescent moiety are measured and recorded simultaneously. The signals are converted to digital form and bundled into a set of measurements associated with each particle.

The bundled measurements may be analyzed to determine the particle specificity and the analyte signal for each particle. The analyte signals from multiple particles of the same class may be combined, for example, by computing the mean value of the analyte signal from each of the beads. Alternatively, various "robust means" algorithms may be employed, such as computing the median value of the analyte signal from each of the particles.

A combined analyte signal from a group of particles of common specificity, which may belong to one or more classes, may be compared to a collection of combined signals from a "standard curve" of signals obtained from the reactions of the calibration samples of a known analyte concentration, and the analyte concentration determined therefrom. Typically, one standard curve is obtained per class of particles; however, the standard curves from more than one class may be combined into a "double standard curve," according to methods known in the art. If there are separate standard curves for the same analyte, guidelines can be provided for determining the result of the assay, e.g., one can use the result from the smaller diameter particles when the result from that class exceeds 100, use the result from the larger diameter particles when the result from that class is less than 10, and use an average of the results from the two classes when the result is between 10 and 100.

Since more than one physical effect governs the amount of signal that develops from the different size particles, the relationship between the expected amount of signal from each particle and the concentration of the analyte is best determined empirically. This may be done by incubating aliquots of the two particle sizes under assay conditions with calibrators of known analyte concentration to obtain a combined standard curve.

The concentration of the unknown sample may be determined by reference to this combined standard curve. At the extremes of the curve, only one particle size will produce a useful signal. That is, the first class of coated particles comprising larger particles will produce a useful signal at a lower analyte concentration and the second class of coated particles comprising smaller particles will produce a useful signal at higher analyte concentrations. In the mid-range of analyte concentration, both particle sizes will produce a useful signal. The analyte concentration may be determined with more precision in this range by using a combined, multiparameter standard curve using values from both particle sizes.

The fluorescent moiety typically employed as a label on the ligand results in a change in the amount of light absorbance (optical density) or emission of the particle when excited by energy of the appropriate wavelength. Suitable fluorophores include, but are not limited to, fluorescein, fluorescein isothiocyanate, rhodamine, phycoerythrin, phycocyanin, allophycocyanin, o-phthalaldehyde label, fluorescamine, tetramethylrhodamine, BODIPY, near infrared dyes, lanthanide chelates, Duochrome, PE Tandem, ultralite 700 and Texas red, cyanine dyes, ring-locked dyes, etc. Other labels suitable for use in this invention include phosphorescent, chemiluminescent, or bioluminescent moieties. When these light-emitting labels are used as dyes, a laser is not required, so that the derivative apparatus employs a fluidics device and a light detector with the appropriate electronics.

The amount of analyte bound to a coated particle is described by:

$$\Gamma_a = c_0 \sqrt{D\tau} \frac{1}{(1+D_a)} \bar{t}$$

where $\Gamma$ is the surface concentration of bound analyte in moles per $cm^2$, $c_o$ is the initial analyte concentration in moles per $cm^3$, D is the analyte diffusion constant in $cm^2$ per second, and $D_a$ is the Damkoehler number (the ratio of the surface capture rate to the diffusion rate) and is calculated as:

$$D_a = \frac{R}{\sqrt{D\tau}}$$

where R is the particle radius, $\tau$ is a time constant calculated as:

$$-\tau = \frac{D}{(k_f \Gamma_0)^2}$$

where $k_f$ is the reaction forward rate constant and $\Gamma_o$ is the surface concentration of the binding partner in moles per $cm^2$, and $\bar{t}$ is the reduced time calculated as $\bar{t}=t/\tau$ where t is the reaction time in seconds.

When the particle diameter is small compared to the characteristic diffusion length of the analyte, the analyte is captured at a constant rate per unit of surface area of the particle. Larger particles capture more analyte molecules than smaller particles. The dependence is on the particle surface area, which varies with the square of particle diameter. If left to go to equilibrium, large and small particles would saturate their available ligands at a similar analyte concentration, but this occurs at different signal levels.

Most practical ligand assays operate far from equilibrium. The limit on their range arises from the limited response of the detector system. A labeled ligand may have a single label attached thereto (typical for small molecules) or it may have a few (e.g., 2–10) labels (typical for antibodies). This invention contemplates the use of small particles that bind to ligands labeled with 100–100,000 fluorescent labels so that, for each binding event, a very large fluorescent signal is generated. The use of a large number of fluorescent moieties, (e.g., a labeled ligand) per binding event (e.g., specific capture of a particle-immobilized analyte or analyte analogue by the labeled ligand) improves detectability for very low concentrations of analyte but limits higher end quantitation by overloading the detector. Signals from large particles will reach the limit of the detection system response at a much lower analyte concentration than those from small particles. Hence, the use of more than one size of particle extends the dynamic range of assays, even when the different size particles are coated with the same binding partner and when the same surface concentration is used.

When particle diameters are large compared to the free diffusion length of the analyte, the assay becomes diffusion-limited. This decreases the difference in signal between different size particles, thereby limiting the effectiveness of this approach. However, since the particles used in the assays of this invention are quite small, this does not frequently occur. Also, even if the assay were diffusion-limited, there would still be a difference in signal, albeit varying only linearly with particle diameter.

The present invention also contemplates a kit containing reagents for carrying out the present inventive method. The kit comprises, in separate containers or premixed, a set comprising a first and second class of particles coated with a binding partner to the analyte of interest. The kit may additionally include a separate container of a ligand labeled with a detectable label, particularly a fluorescent moiety which emits detectable fluorescence upon exposure to excitation energy, wherein the ligand is capable of binding to the sample analyte or to the immobilized binding partner and allows for the detection of the analyte in the sample The assays of this invention can be used to detect analytes in a variety of samples. As used herein, the term "sample" refers to any sample suspected of containing the analyte of interest. The test sample can be untreated (undiluted), or chemically and/or physically treated, diluted, or concentrated prior to analysis. Examples of samples include, but are not limited to, samples from biological sources, such as physiological fluids, including whole blood, plasma, serum, saliva, cerebral spinal fluid, urine, amniotic fluid, urine, feces, mucus, cell or tissue extracts, and any other type of fluid, tissue or material which is suspected of containing an analyte of interest.

The methods of this invention offer several advantages over other methods in the art including: 1) extending the dynamic range of assays without sample dilution and rerun, thereby increasing net system throughput, 2) extending the dynamic range with a single type of capture ligand, thus avoiding the complication of developing multiple capture ligands, and 3) enabling a single ligand-particle coating protocol, thus avoiding the complication of developing alternative protocols with different surface ligand concentrations.

The invention may be embodied in other specific forms without departing from its essential characteristics. The described embodiments are to be considered in all respects only as illustrative and not as restrictive. Indeed, those skilled in the art can readily envision and produce further embodiments, based on the teachings herein, without undue experimentation. The scope of the invention is, therefore, indicated by the appended claims rather than by the foregoing description. All changes that come within the meaning and range of the equivalence of the claims are to be embraced within their scope.

I claim:

1. A method for assaying an analyte in a sample, comprising:
   a) providing a set of coated particles comprising at least
      i) a first class of particles having a first analyte-specific binding partner immobilized thereon, and
      ii) a second class of particles having a second analyte-specific binding partner immobilized thereon, wherein said first and second classes of coated particles are independently determinable, wherein said particles of said first class of particles are smaller than the particles of said second class, and wherein the first binding partner and the second binding partner are the same;
   b) simultaneously incubating said sample in the presence of said set of particles under conditions that allow the formation of a first complex comprising said analyte bound to said first binding partner immobilized on said first class of particles and/or a second complex comprising said analyte bound to said second binding partner immobilized on said second class of particles;
   c) correlating the amount of said first complex and/or said second complex to the concentration of said analyte in said sample; and
   d) determining the concentration of said analyte.

2. The method of claim 1, further comprising providing a labeled ligand comprising a labeled third binding partner for said analyte, and incubating a known amount of said labeled ligand with said set of particles under conditions that allow said labeled ligand to bind to said analyte of said first and/or said second complex, wherein said determination comprises detecting a first and/or a second signal produced by said labeled ligand bound to said analyte of said first and/or said second complex, respectively, wherein said signals are directly related to the concentration of said analyte.

3. The method of claim 2, wherein said concentration is determined by reference to a combined calibration curve.

4. The method of claim 2, wherein said label is selected from the group consisting of fluorescent moieties, phosphorescent moieties, chemiluminescent moieties, or bioluminescent moieties.

5. The method of claim 1, further comprising providing a labeled ligand comprising a labeled analogue of said analyte and incubating a known amount of said labeled ligand with said set of particles, wherein said labeled analogue competes with said analyte for binding said first binding partner to form a third complex comprising said labeled analogue bound to said first binding partner immobilized on said particles of said first class and/or competes with said analyte for binding said second binding partner to form a fourth complex comprising said labeled analogue bound to said second binding partner immobilized on said particles of said second class, wherein said determination comprises detecting a signal produced by said third and/or said fourth complex, wherein said signals are inversely related to the concentration of said sample analyte.

6. The method of claim 5, wherein said concentration is determined by reference to a combined calibration curve.

7. The method of claim 5, wherein said label is selected from the group consisting of fluorescent moieties, phosphorescent moieties, chemiluminescent moieties, or bioluminescent moieties.

8. The method of claim 1, wherein said first and second classes of particles are made from the same type of material.

9. The method of claim 1, wherein said first and second classes of particles are made from different types of material.

10. The method of claim 1, wherein said first and second classes of particles are determinable based on their sizes.

11. The method of claim 1, wherein said first and second classes of particles further comprise first and second distinguishable dyes, respectively.

12. The method of claim 1, wherein the concentration of said analyte is determined by flow cytometry.

13. The method of claim 1, wherein the concentration of said analyte is determined by scanning cytometry.

14. The method of claim 1, wherein the ratio of the diameters of said particles of said first and second particles classes is between about 1:1.4 to 1:4.

15. The method of claim 14, wherein the diameter of said particles of said first class is about 3 micrometers, and the diameter of said particles of said second class is between about 4 and 12 micrometers.

16. The method of claim 1, wherein the amount of analyte that binds to said first or second binding partner is determined by the formula:

$$\Gamma_a = c_0 \sqrt{D\tau} \frac{1}{(1+D_a)} \bar{t}$$

wherein $\Gamma_a$ is the surface concentration of bound analyte in moles/cm²;

$c_o$ is the initial analyte concentration in moles/cm³;

D is the analyte diffusion constant in cm²/s; and $D_a$ is the ratio of the surface capture rate to the diffusion rate.

17. The method of claim 16, wherein $D_a$ is calculated as $$D_a = \frac{R}{\sqrt{D\tau}}$$

wherein R is the particle radius and $\tau$ is calculated as $$-\tau = \frac{D}{(k_f \Gamma_0)^2}$$

where $k_f$ is the reaction forward rate constant, $\Gamma_o$ is the surface concentration of the first or the second binding partner in moles/cm², and t is the reduced time calculated as $$\bar{t} = t/\tau$$

where t is the reaction time in seconds.

18. The method of claim 2, wherein a plurality of analytes is assayed using a predetermined number of sets of distinguishable classes of particles and labeled third binding partners.

19. The method of claim 5, wherein a plurality of analytes is assayed using a predetermined number of sets of distinguishable classes of particles and labeled analyte analogues or labeled analytes.

20. A method for assaying a plurality of analytes in a sample, comprising:

a) providing a plurality of sets of coated particles equal to the number of analytes to be assayed, wherein each set of coated particles is specific for a particular analyte of interest and is separately determinable, wherein each set comprises at least i) a first class of particles having a first binding partner immobilized thereon, and ii) a second class of particles having a second binding partner immobilized thereon, wherein said first and second classes of coated particles are independently determinable, wherein said particles of said first class of particles are smaller than the particles of said second class, and wherein the first binding partner and the second binding partner are the same;

b) simultaneously incubating said sample in the presence of said sets of coated particles under conditions that allow the formation of a set of complexes for each analyte, wherein each set of complexes comprises; a first complex comprising said set-specific analyte bound to said first binding partner immobilized on said first class of particles and/or a second complex comprising said set-specific analyte bound to said second binding partner immobilized on said second class of particles; and c) correlating the amount of said first complex and/or said second complex formed by each set of coated particles to the concentrations of said analytes in said sample; and d) determining the concentration of said analytes.

21. The method of claim 20, further comprising providing a plurality of labeled ligands equal to the number of analytes to be assayed wherein each labeled ligand comprises a third binding partner specific for a particular analyte, and incubating known amounts of said labeled ligands with said sample and said plurality of sets under conditions that allow each of said analytes of said first and/or said second complexes to bind to its specific labeled ligand, wherein said determination comprises detecting a first and/or a second signal produced by said labeled ligand bound to said analyte of said first and/or said second complex, respectively, wherein said signals are directly related to the concentrations of said analytes.

22. The method of claim 21, wherein said label is selected from the group consisting of fluorescent moieties, phosphorescent moieties, chemiluminescent moieties, or bioluminescent moieties.

23. The method of claim 20, further comprising providing a plurality of labeled ligands wherein each ligand comprises a labeled analogue of a particular analyte, and incubating known amounts of said labeled ligands with said sample and said sets of coated particles, wherein said labeled analogues compete with said analytes for binding said first and second binding partners, wherein each of said labeled analogues forms a third complex comprising said labeled analogue bound to said first binding partner on said first particle of said first class and/or a fourth complex comprising said labeled analogue bound to said second binding partner on a particle of said second class, wherein said determination comprises detecting signals produced by each of said third and/or said fourth complexes, wherein said signals are inversely related to the concentrations of said sample analytes.

24. The method of claim 23, wherein said label is selected from the group consisting of fluorescent moieties, phosphorescent moieties, chemiluminescent moieties, or bioluminescent moieties.

25. The method of claim 20, wherein said first and second classes of particles of each set further comprise first and second distinguishable dyes, respectively.

26. The method of claim 20, wherein said first and second classes of particles in each set are made from the same type of material.

27. The method of claim 20, wherein said first and second classes of particles in each set are made from different types of material.

28. The method of claim 20, wherein the concentration of each of said analytes is determined by flow cytometry.

29. The method of claim 20, wherein the concentration of each of said analytes is determined by scanning cytometry.

30. The method of claim 20, wherein the ratio of the diameters of said first and second particles classes in each of said sets is between about 1:1.4 to 1:4.

31. The method of claim 30, wherein the diameter of said particles of said first class is about 3 micrometers and the diameter of said particles of said second class is between about 4 and 12 micrometers.

32. A kit for assaying an analyte in a test sample, said kit comprising:
(a) a set of coated particles comprising at least
   i) a first class of particles having a first analyte-specific binding partner immobilized thereon, and
   ii) a second class of particles having a second analyte-specific binding partner immobilized thereon, wherein said first and second classes of particles are independently determinable, wherein said particles of said first class of particles are smaller than the particles of said second class, and wherein the first binding partner and the second binding partner are the same; and
(b) a labeled ligand, wherein said ligand comprises either a third binding partner for said analyte or an analyte analogue.

33. The kit of claim 32, wherein said first and second classes of particles are contained in the same container means.

34. The kit of claim 32, wherein said first and second classes of particles are contained in separate container means.

35. The kit of claim 32, wherein said label is selected from the group consisting of fluorescent moieties, phosphorescent moieties, chemiluminescent moieties, or bioluminescent moieties.

36. The kit of claim 32, wherein said first and second classes of particles are made from the same type of material.

37. The kit of claim 32, wherein said first and second classes of particles are made from different types of material.

38. The kit of claim 32, wherein said first and second classes of particles are determinable based on their sizes.

39. The kit of claim 32, wherein said first and second classes of particles further comprise first and second distinguishable dyes, respectively.

40. The kit of claim 32, wherein the ratio of the diameters of said particles of said first and second particles classes is between about 1:1.4 to 1:4.

41. The kit of claim 40, wherein the diameter of said first class of particles is about 3 micrometers, and the diameter of said second class of particles is between about 4 and 12 micrometers.

* * * * *